United States Patent
Parker et al.

(10) Patent No.: US 11,045,129 B2
(45) Date of Patent: *Jun. 29, 2021

(54) METHOD AND APPARATUS FOR ESTIMATING NEURAL RECRUITMENT

(71) Applicant: Saluda Medical Pty. Ltd., Artarmon (AU)

(72) Inventors: John Louis Parker, Artarmon (AU); James Hamilton Wah, Artarmon (AU); Dean Michael Karantonis, Artarmon (AU)

(73) Assignee: Saluda Medical Pty Ltd., Artarmon (AU)

( * ) Notice: Subject to any disclaimer, the term of this patent is extended or adjusted under 35 U.S.C. 154(b) by 323 days.

This patent is subject to a terminal disclaimer.

(21) Appl. No.: 15/928,040

(22) Filed: Mar. 21, 2018

(65) Prior Publication Data

US 2018/0256052 A1    Sep. 13, 2018

Related U.S. Application Data

(63) Continuation of application No. 14/117,152, filed as application No. PCT/AU2012/000517 on May 11, 2012, now Pat. No. 9,974,455.

(30) Foreign Application Priority Data

May 13, 2011  (AU) ................................. 2011901817
May 13, 2011  (AU) ................................. 2011901827

(51) Int. Cl.
*A61B 5/24*   (2021.01)
*A61N 1/05*   (2006.01)
*A61N 1/36*   (2006.01)

(52) U.S. Cl.
CPC .............. *A61B 5/24* (2021.01); *A61N 1/0551* (2013.01); *A61N 1/36071* (2013.01); *A61N 1/36135* (2013.01)

(58) Field of Classification Search
CPC .............. A61B 5/4041; A61B 5/04001; A61N 1/0551; A61N 1/36071; A61N 1/36135
See application file for complete search history.

(56) References Cited

U.S. PATENT DOCUMENTS

| 3,736,434 A | 5/1973 | Darrow |
| 3,817,254 A | 6/1974 | Maurer |

(Continued)

FOREIGN PATENT DOCUMENTS

| AU | 2013277009 B2 | 1/2016 |
| CN | 103648583 A | 3/2014 |

(Continued)

OTHER PUBLICATIONS

European Search Report for European Application No. 15861444.6, Search completed Jul. 13, 2018, dated Jul. 23, 2018, 8 pgs.

(Continued)

*Primary Examiner* — Patrick Fernandes
(74) *Attorney, Agent, or Firm* — KPPB LLP

(57) ABSTRACT

An implantable device for estimating neural recruitment arising from a stimulus, has a plurality of electrodes. A stimulus source provides stimuli to be delivered from the electrodes to neural tissue. Measurement circuitry obtains a measurement of a neural signal sensed at the electrodes. A control unit is configured to control application of a selected stimulus to neural tissue using the stimulus electrodes; and after the selected neural stimulus, apply a probe stimulus (Continued)

having a short pulse width. A remnant neural response evoked by the probe stimulus is measured; and the control unit estimates from the remnant neural response a neural recruitment caused by the selected neural stimulus.

14 Claims, 3 Drawing Sheets

(56) References Cited

U.S. PATENT DOCUMENTS

| | | | |
|---|---|---|---|
| 3,898,472 | A | 8/1975 | Long |
| 4,158,196 | A | 6/1979 | Crawford, Jr. |
| 4,418,695 | A | 12/1983 | Buffet |
| 4,474,186 | A | 10/1984 | Ledley et al. |
| 4,628,934 | A | 12/1986 | Pohndorf et al. |
| 4,807,643 | A | 2/1989 | Rosier |
| 4,856,525 | A | 8/1989 | van den Honert |
| 5,113,859 | A | 5/1992 | Funke |
| 5,139,020 | A | 8/1992 | Koestner et al. |
| 5,143,081 | A | 9/1992 | Young et al. |
| 5,156,154 | A | 10/1992 | Valenta, Jr. et al. |
| 5,172,690 | A | 12/1992 | Nappholz et al. |
| 5,184,615 | A | 2/1993 | Nappholz et al. |
| 5,188,106 | A | 2/1993 | Nappholz et al. |
| 5,215,100 | A | 6/1993 | Spitz |
| 5,324,311 | A | 6/1994 | Acken |
| 5,417,719 | A | 5/1995 | Hull et al. |
| 5,431,693 | A | 7/1995 | Schroeppel |
| 5,458,623 | A | 10/1995 | Lu et al. |
| 5,476,486 | A | 12/1995 | Lu et al. |
| 5,497,781 | A | 3/1996 | Chen et al. |
| 5,638,825 | A | 6/1997 | Yamazaki et al. |
| 5,702,429 | A | 12/1997 | King et al. |
| 5,758,651 | A | 6/1998 | Nygard et al. |
| 5,776,170 | A | 7/1998 | MacDonald et al. |
| 5,785,651 | A | 7/1998 | Kuhn et al. |
| 5,792,212 | A | 8/1998 | Weijand et al. |
| 5,814,092 | A | 9/1998 | King |
| 5,913,882 | A | 6/1999 | King |
| 5,999,848 | A | 12/1999 | Gord et al. |
| 6,020,857 | A | 2/2000 | Podger |
| 6,027,456 | A | 2/2000 | Feler et al. |
| 6,038,480 | A | 3/2000 | Hrdlicka et al. |
| 6,066,163 | A | 5/2000 | John |
| 6,114,164 | A | 9/2000 | Dennis et al. |
| 6,144,881 | A | 11/2000 | Hemming et al. |
| 6,157,861 | A | 12/2000 | Faltys et al. |
| 6,212,431 | B1 | 4/2001 | Hahn et al. |
| 6,246,912 | B1 | 6/2001 | Sluijter et al. |
| 6,381,496 | B1 | 4/2002 | Meadows et al. |
| 6,449,512 | B1 | 9/2002 | Boveja |
| 6,463,328 | B1 | 10/2002 | John |
| 6,473,649 | B1 | 10/2002 | Gryzwa et al. |
| 6,473,653 | B1 | 10/2002 | Schallhorn et al. |
| 6,493,576 | B1 | 12/2002 | Dankwart-Eder |
| 6,522,932 | B1 | 2/2003 | Kuzma |
| 6,600,955 | B1 | 7/2003 | Zierhofer et al. |
| 6,658,293 | B2 | 12/2003 | Vonk et al. |
| 6,675,046 | B2 | 1/2004 | Holsheimer |
| 6,782,292 | B2 | 8/2004 | Whitehurst |
| 6,898,582 | B2 | 5/2005 | Lange et al. |
| 7,089,059 | B1 | 8/2006 | Pless |
| 7,171,261 | B1 | 1/2007 | Litvak et al. |
| 7,231,254 | B2 | 6/2007 | DiLorenzo |
| 7,286,876 | B2 | 10/2007 | Yonce et al. |
| 7,412,287 | B2 | 8/2008 | Yonce et al. |
| 7,450,992 | B1 | 11/2008 | Cameron |
| 7,734,340 | B2 | 6/2010 | De Ridder |
| 7,742,810 | B2 | 6/2010 | Moffitt |
| 7,792,584 | B2 | 9/2010 | Van Oort et al. |
| 7,818,052 | B2 | 10/2010 | Litvak et al. |
| 7,831,305 | B2 | 11/2010 | Gliner |
| 7,835,804 | B2 | 11/2010 | Fridman et al. |
| 7,894,905 | B2 | 2/2011 | Pless et al. |
| 8,190,251 | B2 | 5/2012 | Molnar et al. |
| 8,224,459 | B1 | 7/2012 | Pianca et al. |
| 8,239,031 | B2 | 8/2012 | Fried et al. |
| 8,359,102 | B2 | 1/2013 | Thacker et al. |
| 8,417,342 | B1 | 4/2013 | Abell |
| 8,454,529 | B2 | 6/2013 | Daly et al. |
| 8,494,645 | B2 | 7/2013 | Spitzer et al. |
| 8,588,929 | B2 | 11/2013 | Davis et al. |
| 8,670,830 | B2 | 3/2014 | Carlson et al. |
| 8,886,323 | B2 | 11/2014 | Wu et al. |
| 9,155,892 | B2 | 10/2015 | Parker et al. |
| 9,302,112 | B2 | 4/2016 | Bornzin et al. |
| 9,381,356 | B2 | 7/2016 | Parker et al. |
| 9,386,934 | B2 | 7/2016 | Parker et al. |
| 9,872,990 | B2 | 1/2018 | Parker et al. |
| 9,974,455 | B2 | 5/2018 | Parker et al. |
| 10,206,596 | B2 | 2/2019 | Single et al. |
| 10,278,600 | B2 | 5/2019 | Parker et al. |
| 10,368,762 | B2 | 8/2019 | Single |
| 10,426,409 | B2 | 10/2019 | Single |
| 10,500,399 | B2 | 12/2019 | Single |
| 10,568,559 | B2 | 2/2020 | Parker et al. |
| 10,588,524 | B2 | 3/2020 | Single et al. |
| 10,588,698 | B2 | 3/2020 | Parker et al. |
| 10,632,307 | B2 | 4/2020 | Parker |
| 10,849,525 | B2 | 12/2020 | Parker et al. |
| 2002/0055688 | A1 | 5/2002 | Katims |
| 2002/0099419 | A1 | 7/2002 | Ayal et al. |
| 2002/0193670 | A1 | 12/2002 | Garfield et al. |
| 2003/0032889 | A1 | 2/2003 | Wells |
| 2003/0045909 | A1 | 3/2003 | Gross et al. |
| 2003/0139781 | A1 | 7/2003 | Bradley et al. |
| 2003/0153959 | A1 | 8/2003 | Thacker et al. |
| 2003/0195580 | A1 | 10/2003 | Bradley et al. |
| 2004/0088017 | A1 | 5/2004 | Sharma et al. |
| 2004/0122482 | A1 | 6/2004 | Tung et al. |
| 2004/0158298 | A1 | 8/2004 | Gliner |
| 2004/0225211 | A1 | 11/2004 | Gozani et al. |
| 2004/0254494 | A1 | 12/2004 | Spokoyny et al. |
| 2005/0010265 | A1 | 1/2005 | Baru Fassio |
| 2005/0017190 | A1 | 1/2005 | Eversmann et al. |
| 2005/0021104 | A1 | 1/2005 | DiLorenzo |
| 2005/0065427 | A1 | 3/2005 | Magill |
| 2005/0070982 | A1 | 3/2005 | Heruth et al. |
| 2005/0075683 | A1 | 4/2005 | Miesel et al. |
| 2005/0101878 | A1 | 5/2005 | Daly |
| 2005/0113877 | A1 | 5/2005 | Giardiello et al. |
| 2005/0137670 | A1 | 6/2005 | Christopherson et al. |
| 2005/0149154 | A1 | 7/2005 | Cohen |
| 2005/0192567 | A1 | 9/2005 | Katims |
| 2005/0203600 | A1 | 9/2005 | Wallace |
| 2005/0209655 | A1 | 9/2005 | Bradley et al. |
| 2005/0282149 | A1 | 12/2005 | Kovacs et al. |
| 2006/0009820 | A1 | 1/2006 | Royle et al. |
| 2006/0020291 | A1 | 1/2006 | Gozani |
| 2006/0135998 | A1 | 6/2006 | Libbus et al. |
| 2006/0195159 | A1 | 8/2006 | Bradley et al. |
| 2006/0212089 | A1 | 9/2006 | Tass |
| 2006/0217782 | A1 | 9/2006 | Boveja et al. |
| 2006/0264752 | A1 | 11/2006 | Rubinsky et al. |
| 2006/0287609 | A1 | 12/2006 | Litvak et al. |
| 2007/0021800 | A1 | 1/2007 | Bradley et al. |
| 2007/0073354 | A1 | 3/2007 | Knudson et al. |
| 2007/0100378 | A1 | 5/2007 | Maschino |
| 2007/0178579 | A1 | 8/2007 | Ross et al. |
| 2007/0185409 | A1 | 8/2007 | Wu et al. |
| 2007/0208394 | A1 | 9/2007 | King et al. |
| 2007/0225767 | A1 | 9/2007 | Daly et al. |
| 2007/0244410 | A1 | 10/2007 | Fridman et al. |
| 2007/0250120 | A1 | 10/2007 | Flach et al. |
| 2007/0255372 | A1 | 11/2007 | Metzler et al. |
| 2007/0282217 | A1 | 12/2007 | McGinnis et al. |
| 2007/0287931 | A1 | 12/2007 | Dilorenzo |
| 2008/0021292 | A1 | 1/2008 | Stypulkowski |
| 2008/0051647 | A1 | 2/2008 | Wu et al. |
| 2008/0064947 | A1 | 3/2008 | Heruth et al. |
| 2008/0077191 | A1 | 3/2008 | Morrell |
| 2008/0097529 | A1 | 4/2008 | Parramon et al. |
| 2008/0147155 | A1 | 6/2008 | Swoyer |

(56) References Cited

U.S. PATENT DOCUMENTS

| | | |
|---|---|---|
| 2008/0183076 A1 | 7/2008 | Witte et al. |
| 2008/0208304 A1 | 8/2008 | Zdravkovic et al. |
| 2008/0234780 A1 | 9/2008 | Smith et al. |
| 2008/0275527 A1 | 11/2008 | Greenberg et al. |
| 2008/0294221 A1 | 11/2008 | Kilgore |
| 2008/0300655 A1 | 12/2008 | Cholette |
| 2008/0319508 A1 | 12/2008 | Botros et al. |
| 2009/0033486 A1 | 2/2009 | Costantino et al. |
| 2009/0058635 A1 | 3/2009 | Lalonde et al. |
| 2009/0082691 A1 | 3/2009 | Denison et al. |
| 2009/0149912 A1 | 6/2009 | Dacey, Jr. et al. |
| 2009/0157155 A1 | 6/2009 | Bradley |
| 2009/0270957 A1 | 10/2009 | Pianca |
| 2009/0287277 A1 | 11/2009 | Conn et al. |
| 2009/0299214 A1 | 12/2009 | Wu et al. |
| 2009/0306491 A1 | 12/2009 | Haggers |
| 2010/0010388 A1 | 1/2010 | Panken et al. |
| 2010/0058126 A1 | 3/2010 | Chang et al. |
| 2010/0069835 A1 | 3/2010 | Parker |
| 2010/0069996 A1 | 3/2010 | Strahl |
| 2010/0070007 A1 | 3/2010 | Parker |
| 2010/0070008 A1 | 3/2010 | Parker |
| 2010/0100153 A1 | 4/2010 | Carlson et al. |
| 2010/0106231 A1 | 4/2010 | Torgerson |
| 2010/0114237 A1 | 5/2010 | Giftakis et al. |
| 2010/0114258 A1 | 5/2010 | Donofrio et al. |
| 2010/0125313 A1 | 5/2010 | Lee et al. |
| 2010/0125314 A1 | 5/2010 | Bradley et al. |
| 2010/0145222 A1 | 6/2010 | Brunnett et al. |
| 2010/0152808 A1 | 6/2010 | Boggs, II |
| 2010/0179626 A1 | 7/2010 | Pilarski |
| 2010/0191307 A1 | 7/2010 | Fang et al. |
| 2010/0204748 A1 | 8/2010 | Lozano et al. |
| 2010/0222844 A1 | 9/2010 | Troosters et al. |
| 2010/0222858 A1 | 9/2010 | Meloy |
| 2010/0249643 A1 | 9/2010 | Gozani et al. |
| 2010/0249867 A1 | 9/2010 | Wanasek |
| 2010/0258342 A1 | 10/2010 | Parker |
| 2010/0262208 A1 | 10/2010 | Parker |
| 2010/0262214 A1 | 10/2010 | Robinson |
| 2010/0280570 A1 | 11/2010 | Sturm et al. |
| 2010/0286748 A1 | 11/2010 | Midani et al. |
| 2010/0331604 A1 | 12/2010 | Okamoto et al. |
| 2010/0331926 A1 | 12/2010 | Lee et al. |
| 2011/0004207 A1 | 1/2011 | Wallace et al. |
| 2011/0021943 A1 | 1/2011 | Lacour et al. |
| 2011/0028859 A1 | 2/2011 | Chian |
| 2011/0040546 A1 | 2/2011 | Gerber et al. |
| 2011/0077712 A1 | 3/2011 | Killian |
| 2011/0087085 A1 | 4/2011 | Tsampazis et al. |
| 2011/0093042 A1 | 4/2011 | Torgerson et al. |
| 2011/0106100 A1 | 5/2011 | Bischoff |
| 2011/0184488 A1 | 7/2011 | De Ridder et al. |
| 2011/0204811 A1 | 8/2011 | Pollmann-retsch |
| 2011/0224665 A1 | 9/2011 | Crosby et al. |
| 2011/0224749 A1 | 9/2011 | Ben-David et al. |
| 2011/0264165 A1 | 10/2011 | Molnar et al. |
| 2011/0270343 A1 | 11/2011 | Buschman et al. |
| 2011/0307030 A1 | 12/2011 | John |
| 2011/0313310 A1 | 12/2011 | Tomita |
| 2011/0313483 A1 | 12/2011 | Hincapie et al. |
| 2012/0029377 A1 | 2/2012 | Polak |
| 2012/0059275 A1 | 3/2012 | Fagin et al. |
| 2012/0101552 A1 | 4/2012 | Lazarewicz et al. |
| 2012/0109004 A1 | 5/2012 | Cadwell |
| 2012/0109236 A1 | 5/2012 | Jacobson et al. |
| 2012/0155183 A1 | 6/2012 | Aritome |
| 2012/0185020 A1 | 7/2012 | Simon et al. |
| 2012/0253423 A1 | 10/2012 | Youn et al. |
| 2012/0277621 A1 | 11/2012 | Gerber et al. |
| 2012/0277823 A1 | 11/2012 | Gerber et al. |
| 2012/0310301 A1 | 12/2012 | Bennett et al. |
| 2013/0053722 A1 | 2/2013 | Carlson et al. |
| 2013/0060302 A1 | 3/2013 | Polefko et al. |
| 2013/0172774 A1 | 7/2013 | Crowder et al. |
| 2013/0289661 A1 | 10/2013 | Griffith et al. |
| 2013/0289683 A1 | 10/2013 | Parker et al. |
| 2014/0066803 A1 | 3/2014 | Choi |
| 2014/0142447 A1 | 5/2014 | Takahashi et al. |
| 2014/0194771 A1 | 7/2014 | Parker et al. |
| 2014/0194772 A1 | 7/2014 | Single et al. |
| 2014/0236042 A1 | 8/2014 | Parker et al. |
| 2014/0236257 A1 | 8/2014 | Parker et al. |
| 2014/0243926 A1 | 8/2014 | Carcieri |
| 2014/0243931 A1 | 8/2014 | Parker et al. |
| 2014/0249396 A1 | 9/2014 | Shacham-diamand et al. |
| 2014/0276195 A1 | 9/2014 | Papay et al. |
| 2014/0277250 A1 | 9/2014 | Su et al. |
| 2014/0288551 A1 | 9/2014 | Bharmi et al. |
| 2014/0288577 A1 | 9/2014 | Robinson et al. |
| 2014/0296737 A1 | 10/2014 | Parker et al. |
| 2014/0350634 A1 | 11/2014 | Grill et al. |
| 2014/0358024 A1 | 12/2014 | Nelson et al. |
| 2015/0018699 A1 | 1/2015 | Zeng et al. |
| 2015/0025597 A1 | 1/2015 | Surth et al. |
| 2015/0164354 A1 | 6/2015 | Parker et al. |
| 2015/0174396 A1 | 6/2015 | Fisher et al. |
| 2015/0238104 A1 | 8/2015 | Tass |
| 2015/0238304 A1 | 8/2015 | Lamraoui |
| 2015/0282725 A1 | 10/2015 | Single |
| 2015/0313487 A1 | 11/2015 | Single |
| 2015/0360031 A1 | 12/2015 | Bornzin et al. |
| 2015/0374999 A1 | 12/2015 | Parker |
| 2016/0082265 A1 | 3/2016 | Moffitt et al. |
| 2016/0082268 A1 | 3/2016 | Hershey et al. |
| 2016/0106980 A1 | 4/2016 | Sürth et al. |
| 2016/0121124 A1 | 5/2016 | Johanek et al. |
| 2016/0129272 A1 | 5/2016 | Hou et al. |
| 2016/0166164 A1 | 6/2016 | Obradovic et al. |
| 2016/0175594 A1 | 6/2016 | Min et al. |
| 2016/0287126 A1 | 10/2016 | Parker et al. |
| 2016/0287182 A1 | 10/2016 | Single |
| 2016/0367808 A9 | 12/2016 | Simon et al. |
| 2017/0001017 A9 | 1/2017 | Parker et al. |
| 2017/0049345 A1 | 2/2017 | Single |
| 2017/0071490 A1 | 3/2017 | Parker et al. |
| 2017/0135624 A1 | 5/2017 | Parker |
| 2017/0216587 A1 | 8/2017 | Parker |
| 2017/0361101 A1 | 12/2017 | Single |
| 2018/0110987 A1 | 4/2018 | Parker |
| 2018/0117335 A1 | 5/2018 | Parker et al. |
| 2018/0132747 A1 | 5/2018 | Parker et al. |
| 2018/0132760 A1 | 5/2018 | Parker |
| 2018/0133459 A1 | 5/2018 | Parker et al. |
| 2018/0228391 A1 | 8/2018 | Parker et al. |
| 2018/0228547 A1 | 8/2018 | Parker |
| 2018/0229046 A1 | 8/2018 | Parker et al. |
| 2019/0168000 A1 | 6/2019 | Laird-wah |
| 2019/0216343 A1 | 7/2019 | Single et al. |
| 2019/0239768 A1 | 8/2019 | Karantonis et al. |
| 2019/0307341 A1 | 10/2019 | Parker et al. |
| 2019/0357788 A1 | 11/2019 | Single |
| 2020/0029914 A1 | 1/2020 | Single |
| 2020/0129108 A1 | 4/2020 | Parker et al. |
| 2020/0155240 A1 | 5/2020 | Parker et al. |
| 2020/0215331 A1 | 7/2020 | Single |
| 2020/0282208 A1 | 9/2020 | Parker |

FOREIGN PATENT DOCUMENTS

| | | |
|---|---|---|
| CN | 103654762 A | 3/2014 |
| CN | 103842022 A | 6/2014 |
| CN | 104411360 A | 3/2015 |
| EP | 0219084 | 4/1987 |
| EP | 0998958 B1 | 8/2005 |
| EP | 2019716 A | 11/2007 |
| EP | 2243510 A2 | 10/2010 |
| EP | 2443995 A2 | 4/2012 |
| EP | 2707095 A1 | 3/2014 |
| EP | 3229893 A1 | 10/2017 |
| JP | 2006504494 A | 2/2006 |
| JP | 2009512505 A | 3/2009 |
| JP | 2012524629 | 10/2012 |
| JP | 2013527784 A | 7/2013 |

(56) References Cited

FOREIGN PATENT DOCUMENTS

| | | |
|---|---|---|
| JP | 2013536044 A | 9/2013 |
| JP | 2014522261 A | 9/2014 |
| JP | 2014523261 A | 9/2014 |
| WO | 1983003191 A | 9/1983 |
| WO | 1993001863 A1 | 2/1993 |
| WO | 1996012383 A1 | 4/1996 |
| WO | 2000002623 A1 | 1/2000 |
| WO | 2002036003 A1 | 11/2001 |
| WO | 2002038031 | 5/2002 |
| WO | 2002049500 A2 | 6/2002 |
| WO | 2003028521 A2 | 4/2003 |
| WO | 2003043690 | 5/2003 |
| WO | 2003103484 | 12/2003 |
| WO | 2004021885 A1 | 3/2004 |
| WO | 2004103455 | 12/2004 |
| WO | 2005032656 A1 | 4/2005 |
| WO | 2005105202 A1 | 11/2005 |
| WO | 2006091636 A2 | 8/2006 |
| WO | 2007050657 A1 | 5/2007 |
| WO | 2007064936 A1 | 6/2007 |
| WO | 2007127926 A2 | 11/2007 |
| WO | 2007130170 A1 | 11/2007 |
| WO | 2008004204 A1 | 1/2008 |
| WO | 2008049199 A1 | 5/2008 |
| WO | 2009002072 A2 | 12/2008 |
| WO | 2009002579 A1 | 12/2008 |
| WO | 2009010870 A2 | 1/2009 |
| WO | 2009130515 A2 | 10/2009 |
| WO | 2009146427 A1 | 12/2009 |
| WO | 2010013170 A1 | 2/2010 |
| WO | 2010044989 A2 | 4/2010 |
| WO | 2010051392 A1 | 5/2010 |
| WO | 2010057046 A2 | 5/2010 |
| WO | 2010124139 A1 | 10/2010 |
| WO | 2010138915 A1 | 12/2010 |
| WO | 2011011327 A1 | 1/2011 |
| WO | 2011066477 A1 | 6/2011 |
| WO | 2011066478 A1 | 6/2011 |
| WO | 2011112843 A1 | 9/2011 |
| WO | 2011119251 A2 | 9/2011 |
| WO | 2011159545 A2 | 12/2011 |
| WO | 2012027252 A2 | 3/2012 |
| WO | 2012027791 A1 | 3/2012 |
| WO | 2012155183 A1 | 11/2012 |
| WO | 2012155184 A1 | 11/2012 |
| WO | 2012155185 A1 | 11/2012 |
| WO | 2012155187 A1 | 11/2012 |
| WO | 2012155188 A1 | 11/2012 |
| WO | 2012155189 A1 | 11/2012 |
| WO | 2012155190 A1 | 11/2012 |
| WO | 2013063111 A1 | 5/2013 |
| WO | 2013075171 A1 | 5/2013 |
| WO | 2014071445 A1 | 5/2014 |
| WO | 2014071446 A1 | 5/2014 |
| WO | 2014143577 A1 | 9/2014 |
| WO | 2015070281 A1 | 5/2015 |
| WO | 2015074121 A1 | 5/2015 |
| WO | 2015109239 A1 | 7/2015 |
| WO | 2015143509 A1 | 10/2015 |
| WO | 2015168735 A1 | 11/2015 |
| WO | 2016011512 | 1/2016 |
| WO | 2016059556 A1 | 4/2016 |
| WO | 2016077882 A1 | 5/2016 |
| WO | 2016090420 A1 | 6/2016 |
| WO | 2016090436 A1 | 6/2016 |
| WO | 2016115596 A1 | 7/2016 |
| WO | 2016161484 A2 | 10/2016 |
| WO | 2016191807 A1 | 12/2016 |
| WO | 2016191808 A1 | 12/2016 |
| WO | 2016191815 A1 | 12/2016 |
| WO | 2017173493 A1 | 10/2017 |
| WO | 2017219096 A1 | 12/2017 |
| WO | 2019178634 A1 | 9/2019 |
| WO | 2019204884 A1 | 10/2019 |

OTHER PUBLICATIONS

Extended European Search Report for European Application No. 16739680.3, Search completed Jun. 1, 2018, dated Jun. 12, 2018, 9 pgs.

International Search Report and Written Opinion for International Application No. PCT/AU2017/050296, Search completed Jul. 28, 2017, dated Jul. 28, 2017, 10 pgs.

Partial European Search Report for European Application No. 16775966.1, Search completed Oct. 26, 2018, dated Nov. 6, 2018, 11 Pgs.

French et al., "Information transmission at 500 bits/s by action potentials in a mechanosensory neuron of the cockroach", Neuroscience Letters, vol. 243, No. 1-3, Feb. 1, 1998, pp. 113-116.

He et al., "Perception threshold and electrode position for spinal cord stimulation", Pain, 59 (1994) 55-63 pages.

Herreras, "Local Field Potentials: Myths and Misunderstandings", Frontiers in Neural Circuits, Dec. 15, 2016, vol. 10, Article 1101, 16 pgs.

Holsheimer et al., "Significance of the Spinal Cord Position in Spinal Cord Stimulation", Acta Neurochir (1995) [Suppl] 64: 119-124 pages.

Holsheimer et al., "Spinal Geometry and Paresthesia Coverage in Spinal Cord Stimulation", (1998 paper) 8 pages.

Olin et al., "Postural Changes in Spinal Cord Stimulation Perceptual Thresholds", Neuromodulation, vol. 1, No. 4, 1998, pp. 171-175.

Rattay, "Analysis of Models for External Stimulation of Axons", IEEE Transactions on Biomedical Engineering, vol. BME-33, No. 10, Oct. 1986, pp. 974-977.

Ross et al., "Improving Patient Experience with Spinal Cord Stimulation: Implications of Position-Related Changes in Neurostimulation", Neuromodulation 2011; e-pub ahead of print. DOI: 10.1111/j.1525-1403.2011.00407.x 6 pages.

Struijk, "The Extracellular Potential of a Myelinated Nerve Fiber in an Unbounded Medium and in Nerve Cuff Models", Biophysical Journal vol. 72, Jun. 1997, pp. 2457-2469.

Extended European Search Report for European Application No. 16802237.4, Search completed Dec. 11, 2018, dated Dec. 19, 2018, 9 Pgs.

Extended European Search Report for European Application No. 16802238.2, Search completed Oct. 17, 2018, dated Oct. 24, 2018, 8 Pgs.

International Preliminary Report for International Application No. PCT/AU2017/050647, dated Dec. 25, 2018, 8 pgs.

International Search Report and Written Opinion for International Application No. PCT/AU2017/050647, Search completed Sep. 29, 2017, dated Sep. 29, 2017, 13 Pgs.

Bahmer et al., "Application of triphasic pulses with adjustable phase amplitude ratio (PAR) for cochlear ECAP recording: I. Amplitude growth functions", Journal of Neuroscience Methods, Clinical Neuroscience, 2012, vol. 205, pp. 202-211.

Bahmer et al., "Effects of electrical pulse polarity shape on intra cochlear neural responses in humans: Triphasic pulses with cathodic second phase", Hearing Research, 2013, vol. 306, pp. 123-130.

Gnadt et al., "Spectral Cancellation of Microstimulation Artifact for Simultaneous Neural Recording In Situ", IEEE Transactions on Biomedical Engineering, Oct. 2003, Date of Publication: Sep. 23, 2003, vol. 50, No. 10, pp. 1129-1135, DOI: 10.1109/TBME.2003. 816077.

Jeffrey et al., "A reliable method for intracranial electrode implantation and chronic electrical stimulation in the mouse brain", BMC Neuroscience Biomed Central. London. GB. vol. 14. No. 1. Aug. 6, 2013 (Aug. 6, 2013) • p. 82.

Tronnier et al., "Magnetic Resonance Imaging with Implanted Neurostimulators: An In Vitro and In Vlvo Study", Jannuary 1999, Neurosurgery, vol. 44(1), p. 118-125 (Year: 1999).

International Preliminary Report for International Application No. PCT/AU2017/050296, dated Oct. 9, 2018, 7 Pgs.

International Preliminary Report on Patentability for International Application No. PCT/AU2015/050787, report dated Jun. 13, 2017, 6 pgs.

(56) References Cited

OTHER PUBLICATIONS

International Preliminary Report on Patentability for International Application No. PCT/AU2016/050019, report dated Jul. 25, 2017, 9 pgs.
International Preliminary Report on Patentability for International Application No. PCT/AU2016/050263, report dated Oct. 10, 2017, 9 pgs.
International Search Report & Written Opinion for International Application No. PCT/AU2013/001280, completed Jan. 16, 2014, dated Jan. 16, 2014, 8 pgs.
International Search Report & Written Opinion for International Application PCT/AU2013/001279, completed Jan. 9, 2014, dated Jan. 9, 2014, 9 pgs.
International Search Report and Written Opinion for International Application No. PCT/AU2011/001127, completed Nov. 11, 2011, dated Nov. 15, 2011, 13 pgs.
International Search Report and Written Opinion for International Application No. PCT/AU2012/001441, completed Feb. 26, 2013, dated Feb. 26, 2013, 14 pgs.
International Search Report and Written Opinion for International Application No. PCT/AU2014/001049, completed Feb. 10, 2015, dated Feb. 10, 2015, 8 pgs.
International Search Report and Written Opinion for International Application No. PCT/AU2014/050369, completed Feb. 20, 2015, dated Feb. 20, 2015, 14 pgs.
International Search Report and Written Opinion for International Application No. PCT/AU2015/050135, completed Jun. 30, 2015, dated Jun. 30, 2015, 26 pgs.
International Search Report and Written Opinion for International Application No. PCT/AU2015/050422, completed Oct. 14, 2015, dated Oct. 14, 2015, 17 pgs.
International Search Report and Written Opinion for International Application No. PCT/AU2015/050724, completed May 9, 2016, dated May 9, 2016, 8 pgs.
International Search Report and Written Opinion for International Application No. PCT/AU2015/050753, completed Feb. 10, 2016, dated Feb. 10, 2016, 10 pgs.
International Search Report and Written Opinion for International Application No. PCT/AU2015/050787, completed Mar. 16, 2016, dated Mar. 16, 2016, 10 pgs.
International Search Report and Written Opinion for International Application No. PCT/AU2016/050019, completed May 4, 2016, dated May 4, 2016, 16 pgs.
International Search Report and Written Opinion for International Application No. PCT/AU2016/050263, completed Nov. 16, 2016, dated Nov. 16, 2016, 8 pgs.
International Search Report and Written Opinion for International Application No. PCT/AU2016/050430, completed Aug. 16, 2016, dated Aug. 16, 2016, 10 pgs.
International Search Report and Written Opinion for International Application No. PCT/AU2016/050431, completed Aug. 16, 2016, dated Aug. 16, 2016, 11 pgs.
International Search Report and Written Opinion for International Application No. PCT/AU2016/050439, completed Jul. 15, 2016, dated Jul. 15, 2016, 8 pgs.
International Search Report and Written Opinion for International Application No. PCT/AU2015/050215, completed Jul. 30, 2015, dated Jul. 30, 2015, 8 Pgs.
International Search Report for Australian Application 2011901829, completed Feb. 6, 2012, dated Feb. 7, 2012, 3 pgs.
International Search Report for International Application No. PCT/AU2012/000511, completed May 17, 2012, dated May 18, 2012, 4 pgs.
International Search Report for International Application No. PCT/AU2012/000512, completed Jul. 10, 2012, dated Jul. 11, 2012, 4 pgs.
International Search Report for International Application No. PCT/AU2012/000513, completed May 29, 2012, dated May 30, 2012, 5 pgs.
International Search Report for International Application No. PCT/AU2012/000515, completed May 21, 2012, dated Jun. 4, 2012, 5 pgs.
International Search Report for International Application No. PCT/AU2012/000516, completed Jul. 11, 2012, dated Jul. 12, 2012, 8 pgs.
International Search Report for International Application No. PCT/AU2012/000517, completed Jun. 4, 2012, dated Jun. 6, 2012, 3 pgs.
International Search Report for International Application No. PCT/AU2012/000518, completed Jun. 8, 2012, dated Jun. 12, 2012, 4 pgs.
International Type Search Report for International Application No. AU 2015902393, completed May 16, 2016, dated May 16, 2016, 8 pgs.
Medtronic, Spinal Cord Stimulation, RestoreSensor Neurostimulator, Features and Specification: Specification, Printed Jun. 16, 2014, 2 pgs.
Medtronic, Spinal Cord Stimulation, RestoreSensor Neurostimulator, Features and Specification: Summary Printed Jun. 16, 2014, 1 pg.
Written Opinion for International Application No. PCT/AU2012/000511, completed May 17, 2012, dated May 18, 2012, 5 pgs.
Written Opinion for International Application No. PCT/AU2012/000512, completed Jul. 10, 2012, dated Jul. 11, 2012, 7 pgs.
Written Opinion for International Application No. PCT/AU2012/000513, completed May 29, 2012, dated May 30, 2012, 10 pgs.
Written Opinion for International Application No. PCT/AU2012/000515, completed May 21, 2012, dated Jun. 4, 2012, 4 pgs.
Written Opinion for International Application No. PCT/AU2012/000516, completed Jul. 11, 2012, dated Jul. 12, 2012, 8 pgs.
Written Opinion for International Application No. PCT/AU2012/000517, completed Jun. 4, 2012, dated Jun. 6, 2012, 5 pgs.
Written Opinion for International Application No. PCT/AU2012/000518, completed Jun. 8, 2012, dated Jun. 12, 2012, 10 pgs.
Medtronic, RestoreSensor Neurostimulator, Retrieved from: http://web.archive.org/web/20150328092923/http://professional.medtronic.com:80/pt/neuro/scs/prod/restore-sensor/features-specifications/index.htm,, Capture Date Jul. 9, 2012, Printed on May 11, 2017.
"Advanced Pain Therapy using Neurostimulation for Chronic Pain", Medtronic RestoreSensor clinical trial paper,Clinical summary, Nov. 2011, p. 32.
"Battelle Neurotechnology—Moving Beyond The Limits in Neurotechnology", Battelle, www.battelle.org, May 2014, pp. 1-2.
"Haptic technology", Wkipedia, Retrieved from: http://en.wikipedia.org/wiki/Haptic_technology, Last modified on Sep. 15, 2014, printed on Sep. 15, 2014, 5 pgs.
"Implants for surgery, Cardiac pacemakers", IS-1 standard ISO 5841-3-2000, Oct. 15, 2000.
"Neural Bypass Technology Enables Movement in Paralyzed Patient", Posted on Jul. 29, 2014, 6 a.m. in Brain chips/computer interface, pp. 1-2.
"Spinal Cord Stimulation, About Spinal Cord Stimulation", Medtronic, Retrieved from: http://professional.medtronic.com/pt/neuro/scs/edu/about/index.htm, Printed on Jun. 16, 2014, 2 pgs.
"Wide bandwidth BioAmplifier", http://www.psylab.com/html/default_bioamp.htm, Printed Jan. 30, 2014, pp. 1-3.
Alam et al., "Evaluation of optimal electrode configurations for epidural spinal cord stimulation in cervical spinal cord injured rats", Journal of Neuroscience Methods, Mar. 2015, 28 pgs.
Al-Ani et al., "Automatic removal of high-amplitude stimulus artefact from neuronal signal recorded in the subthalamic nucleus", Journal of Neuroscience Methods, vol. 198, Issue 1, 2011, pp. 135-146.
Massachusetts Institute of Technology, "The Compound Action Potential of the Frog Sciatic Nerve", Quantitative Physiology: Cells and Tissues. Fall, 1999, Retrieved from http://umech.mit.edu/freeman/6.021J/2001/lab.pdf on May 22, 2012.
Matzner et al., "Na+ Conductance and the Threshold for Repetitive Neuronal Firing", Brain Research 597, No. 1 (Nov. 27, 1992): 92-98, doi:10.1016/0006-8993(92)91509-D.
McGill, Kevin et al., "On the Nature and Elimination of Stimulus Artifact in Nerve Signals Evoked and Recorded Using Surface

(56) References Cited

OTHER PUBLICATIONS

Electrodes", IEEE Transactions on Biomedical Engineering, vol. BME-29, No. 2, Feb. 1982, pp. 129-137.
Melzack et al., "Pain mechanisms: a new theory", Science, New York, New York, vol. 150, No. 3699, Nov. 19, 1965, pp. 971-979.
Miles et al., "An Electrode for Prolonged Stimulation of the Brain", Proc. 8th Meeting World Soc. Stereotactic and Functional Neurosurgery, Part III, Zurich, 1981, Appl. Neurophysiol, 45, 1982, pp. 449-445.
Misawa et al., "Neuropathic Pain Is Associated with Increased Nodal Persistent Na(+) Currents in Human Diabetic Neuropathy", Journal of the Peripheral Nervous System: JPNS, 14, No. 4 (Dec. 2009), pp. 279-284.
Nordin et al., "Ectopic Sensory Discharges and Paresthesiae in Patients with Disorders of Peripheral Nerves, Dorsal Roots and Dorsal Columns", Pain 20, No. 3 (Nov. 1984): 231-245, doi:10.1016/0304-3959(84)90013-7.
Oakley et al., "Spinal Cord Stimulation: Mechanisms of Action", Spine 27, No. 22, Nov. 15, 2002, pp. 2574-2583.
Oakley et al., "Transverse Tripolar Spinal Cord Stimulation: Results of an International Multicenter Study", Neuromodulation, vol. 9, No. 3, 2006, pp. 192-203.
Obradovic et al., "Effect of pressure on the spinal cord during spinal cord stimulation in an animal model", Poster, 18th Annual Meeting of the North American Neuromodulation Society, Dec. 11-14, 2014, Las Vegas.
Oh et al., "Long-term hardware-related complications of deep brain stimulation", Neurosurgery, vol. 50, No. 6, Jun. 2002, pp. 1268-1274, discussion pp. 1274-1276.
Opsommer, E. et al. "Determination of Nerve Conduction Velocity of C-fibres in Humans from Thermal Thresholds to Contact Heat (Thermode) and from Evoked Brain Potentials to Radiant Heat (CO2 Laser)", Neurophysiologie Clinique 1999, vol. 29, pp. 411-422.
Orstavik, Kristin et al. "Pathological C-fibres in patients with a chronic painful condition", Brain (2003), 126, 567-578.
Ouyang et al., "Compression Induces Acute Demyelination and Potassium Channel Exposure in Spinal Cord", Journal of Neurotrauma 27, No. 6, Jun. 2010, pp. 1109-1120, doi:10.1089/neu.2010.1271.
Parker et al., "Closing the Loop in Neuromodulation Therapies: Spinal Cord Evoked Compound Action Potentials During Stimulation for Pain Management (230).", 2011, In 15th Annual Meeting, North American Neuromodulation Society (p. 48). Presented at the North American Neuromodulation Society, Las Vegas.
Parker et al., "Compound Action Potentials Recorded in the Human Spinal Cord During Neurostimulation for Pain Relief", Pain, vol. 153, 2012, pp. 593-601.
Parker et al., "Electrically Evoked Compound Action Potentials Recorded. From the Sheep Spinal Cord", Neuromodulation, vol. 16, 2013, pp. 295-303.
Penar et al., "Cortical Evoked Potentials Used for Placement of a Laminotomy Lead Array: A Case Report", Neuromodulation: Technology at the Neural Interface, accessed Apr. 19, 2011, doi:10.1111/j.1525-1403.2011.00352.x.
Richter et al., "EMG and SSEP Monitoring During Cervical Spinal Cord Stimulation", Journal of Neurosurgical Review 2011, Southern Academic Press, 1(S1), 2011, pp. 61-63.
Ridder et al., "Burst Spinal Cord Stimulation for Limb and Back Pain", World Neurosurgery, 2013, 9 pgs.
Ridder et al., "Burst Spinal Cord Stimulation toward Paresthesia-Free Pain Suppression", May 2010, vol. 66, pp. 986-990.
Roy, S. H. et al., "Effects of Electrode Location on Myoelectric Conduction Velocity and Median Frequency Estimates", J. Appl. Physiol. 61 (4), 1986, pp. 1510-1517.
Sayenko et al., "Neuromodulation of evoked muscle potentials induced by epidural spinal-cord stimulation in paralyzed individuals", Journal of Neurophysiology, vol. 111, No. 5, 2014, pp. 1088-1099, First published Dec. 11, 2013.
Schmidt et al., "Gating of tactile input from the hand", Exp Brain Res, 1990, 79, pp. 97-102.

Siegfried et al., "Bilateral Chronic Electrostimulation of Ventroposterolateral Pallidum: A New Therapeutic Approach for Alleviating all Parkinsonian Symptoms", Neurosurgery, 35, No. 6, Dec. 1994, pp. 1126-1130.
Siegfried et al., "Intracerebral Electrode Implantation System", Journal of Neurosurgery, vol. 59, No. 2, Aug. 1983, pp. 356-3591.
Srinivasan, S, "Electrode/Electrolyte Interfaces: Structure and Kinetics of Charge Transfer", Fuel Cells, 2006, Chapter 2, 67 pgs.
Struijk et al, "Paresthesia Thresholds in Spinal Cord Stimulation: A Comparison of Theoretical Results with Clinical Data", IEEE Transactions on Rehabilitation Engineering, vol. 1, No. 2, Jun. 1993, pp. 101-108.
Struijk et al., "Excitation of Dorsal Root Fibers in Spinal Cord Stimulation: a Theoretical Study", IEEE Transactions on Biomedical Engineering, Jul. 1993, vol. 40, No. 7, pp. 632-639.
Sufka et al., "Gate Control Theory Reconsidered", Brain and Mind, 3, No. 2, 2002, pp. 277-290.
Tamura et al., "Increased Nodal Persistent Na+ Currents in Human Neuropathy and Motor Neuron Disease Estimated by Latent Addition", Clinical Neurophysiology 117, No. 11 (Nov. 2006), pp. 2451-2458, doi:10.1016/j.clinph.2006.07.309.
Tasker, "Deep Brain Stimulation is Preferable to Thalamotomy for Tremor Suppression", Surgical Neurology, 49, No. 2, 1998, pp. 145-153.
Taylor et al., "Spinal Cord Stimulation for Chronic Back and Leg Pain and Failed Back Surgery Syndrome: A Systematic Review and Analysis of Prognostic Factors", SPINE, vol. 30, No. 1, 2004, pp. 152-160.
Texas Instruments, "Precision, Low Power Instrumentation Amplifiers", Texas Instruments SBOS051B Oct. 1995, Revised Feb. 2005, 20 pgs.
Tomas et al., "Dorsal Root Entry Zone (DREZ) Localization Using Direct Spinal Cord Stimulation Can Improve Results of the DREZ Thermocoagulation Procedure for Intractable Pain Relief", Pain, 2005, vol. 116, pp. 159-163.
Tscherter et al., "Spatiotemporal Characterization of Rhythmic Activity in Rat Spinal Cord Slice Cultures", European Journal of Neuroscience 14, No. 2 (2001), pp. 179-190.
Van Den Berg et al., "Nerve fiber size-related block of action currents by phenytoin in mammalian nerve", Epilepsia, Nov. 1994, 35(6), pp. 1279-1288.
Villavicencio, Alan T., "Laminectomy versus Percutaneous Electrode Placement for Spinal Cord Stimulation," Neurosurgery, vol. 46 (2), Feb. 2000, pp. 399-405.
Vleggeert et al., Lankamp "Electrophysiology and morphometry of the Aalpha- and Abeta-fiber populations in the normal and regenerating rat sciatic nerve", Experimental Neurology, vol. 187, No. 2, Jun. 1, 2004, Available online Apr. 2, 2004, pp. 337-349.
Woessner, "Blocking Out the Pain, Electric Nerve Block Treatments for Sciatic Neuritis", Retrieved from: http://www.practicalpainmanagement.com/pain/spine/radiculopathy/blocking-out-pain, Last updated Jan. 10, 2012.
Wolter et al., "Effects of sub-perception threshold spinal cord stimulation in neuropathic pain: A randomized controlled double-blind crossover study", European Federation of International Association for the Study of Pain Chapters, 2012, pp. 648-655.
Wu et al., "Changes in Aβ Non-nociceptive Primary Sensory Neurons in a Rat Model of Osteoarthritis Pain", Molecular Pain 6, No. 1 (Jul. 1, 2010): 37, doi:10.1186/1744-8069-6-37.
Xie et al., "Functional Changes in Dorsal Root Ganglion Cells after Chronic Nerve Constriction in the Rat", Journal of Neurophysiology 73, No. 5 (May 1, 1995), pp. 1811-1820.
Xie et al., "Sinusoidal Time-Frequency Wavelet Family and its Application in Electrograstrographic Signal Analysis", Proceedings of the 20th Annual International Conference of the IEEE Engineering in Medicine and Biology Society, vol. 20, No. 3, Oct. 29, 1998, pp. 1450-1453.
Yamada et al., "Extraction and Analysis of the Single Motor Unit F-Wave of the Median Nerve", EMG Methods for Evaluating Muscle and Nerve Function, InTech, 2012, 15 pgs.
Yearwood, T. L., "Pulse Width Programming in Spinal Cord Stimulation: a Clinical Study", Pain Physician. 2010. vol. 13, pp. 321-335.

(56) References Cited

OTHER PUBLICATIONS

Yingling et al., "Use of Antidromic Evoked Potentials in Placement of Dorsal Cord Disc Electrodes", Applied Neurophysiology, 1986, vol. 49, pp. 36-41.
Yuan, S. et al., "Recording monophasic action potentials using a platinum-electrode ablation catheter", Europace. Oct. 2000; 2(4):312-319.
Andreassen, S. et al., "Muscle Fibre Conduction Velocity in Motor Units of the Human Anterior Tibial Muscle: a New Size Principle Parameter", J. Physiol, (1987), 391, pp. 561-571.
Andy, "Parafascicular-Center Median Nuclei Stimulation for Intractable Pain and Dyskinesia (Painful-Dyskinesia)", Stereotactic and Functional Neurosurgery, Appl. Neurophysiol., 43, No. 3-5, 1980, pp. 133-144.
Balzer et al., "Localization of cervical and cervicomedullary stimulation leads for pain treatment using median nerve somatosensay evoked potential collision testing", Journal of Neurosurgery, Jan. 2011, vol. 114, No. 1, pp. 200-205.
Blum, A. R., "An Electronic System for Extracellular Neural Stimulation and Recording", Dissertation, Georgia Institute of Technology, Aug. 2007, Retrieved from http://smartech.gatech.edu/handle/1853/16192 on Jan. 30, 2012.
Borg et al., "Conduction velocity and refractory period of single motor nerve fibres in antecedent poliomyelitis", Journal of Neurology, Neurosurgery, and Psychiatry, vol. 50, 1987, 443-446.
Brown et al., "Impact of Deep Brain Stimulation on Upper Limb Askinesia in Parkinson's Disease", Annals of Neurology, 45, No. 4, 1999, pp. 473-488.
Budagavi et al., "Modelling of compound nerve action potentials health and disease", Engineering in Medicine and Biology Society, 1992 14th Annual International Conference of the IEEE. vol. 6. IEEE, 1992, pp. 2600-2601.
Coquery et al., "Backward and forward masking in the perception of cutaneous stimuli", Perception & Psychophysics, 1973, vol. 13.No. 2, pp. 161-163.
Dawson, G. D., "The relative excitability and conduction velocity of sensory and motor nerve fibres in man", Journal of Physiology, 1956, vol. 131(2), pp. 436-451.
Devergnas et al., A "Cortical potentials evoked by deep brain stimulation in the subthalamic area", Front Syst Neurosci. 2011; 5:30. May 13, 2011. doi:10.3389/fnsys.2011.00030.
Dijkstra, E. A., "Ultrasonic Distance Detection for a Closed-Loop Spinal Cord Stimulation System", Proceedings—19th International Conference—IEEE/EMBS Oct. 30-Nov. 2, 1997, Chicago, IL, 4 pgs.
Dillier, N et al., "Measurement of the electrically evoked compound action potential via a neural response telemetry system", Ann. Otol. Rhinol. Laryngol., vol. 111, No. 5, May 2002, pp. 407-414.
Doiron et al., "Persistent Na+ Current Modifies Burst Discharge by Regulating Conditional Backpropagation of Dendritic Spikes", Journal of Neurophysiology 89, No. 1 (Jan. 1, 2003), pp. 324-337, doi:10.1152/jn.00729.2002.
England et al., "Increased Number of Sodium Channels Form Along Demyelinated Axons", Brain Research 548, No. 1-2 (May 10, 1991), pp. 334-337.
Fagius, J. et al., "Sympathetic Reflex Latencies and Conduction Velocities in Normal Man", Journal of Neurological Sciences, 1980, vol. 47, pp. 433-448.
Falowski et al., "Spinal Cord Stimulation: an update", Neurotherapeutics: The Journal of the American Society for Experimental NeuroTherapeutics 5, No. 1, Jan. 2008, pp. 86-99.
Fisher, "F-Waves—Physiology and Clinical Uses", TheScientificWorldJournal, (2007) 7, pp. 144-160.
Franke et al., FELIX, "An Online Spike Detection and Spike Classification Algorithm Capable of Instantaneous Resolution of Overlapping Spikes", Journal of Computational Neuroscience, 2010, vol. 29, No. 1-2, pp. 127-148.
Fuentes et al., "Spinal Cord Stimulation Restores Locomotion in Animal Models of Parkinson's Disease", Science, vol. 323, No. 5921, Mar. 20, 2009, pp. 1578-1582.
Gad et al., "Development of a multi-electrode array for spinal cord epidural stimulation to facilitate stepping and standing after a complete spinal cord injury in adult rats", Journal of NeuroEngineering and Rehabilitation 2013, 10:2, 18 pgs.
George et al., "Vagus nerve stimulation: a new tool for brain research and therapy", Biological Psychiatry 47, No. 4, Feb. 15, 2000, pp. 287-295.
Goodall, E. V., "Modeling Study of Activation and Propagation delays During Stimulation of Peripheral Nerve Fibres with a Tripolar Cuff Electrode", IEEE Transactions on Rehabilitation Engineering, vol. 3, No. 3, Sep. 1995, pp. 272-282.
Gorman et al., "ECAP Mapping of the Spinal Cord: Influence of Electrode Position on Aβ Recruitment", (2012).,In 16th Annual Meeting. Presented at the North American Neuromodulation Society, Las Vegas, NV.
Gorman et al., "Neural Recordings for Feedback Control of Spinal Cord Stimulation: Reduction of Paresthesia Variability.", 2013,In International Neuromodulation Society 11th World Congress. Presented at the International Neuromodulation Society 11th World Congress, Berlin, Germany.
Hallstrom et al, "Distribution of lumbar spinal evoked potentials and their correlation with stimulation-induced paresthesiae", (1991), Electroencephalography and Clinical Neurophysiology 80:126-139.
Harper, A. A. et al., "Conduction Velocity is Related to Morphological Cell Type in Rat Dorsal Root Ganglion Neurones", J. Physiol, (1985), 359, pp. 31-46.
Holsheimer et al., "Optimum Electrode Geometry for Spinal Cord Stimulation: the Narrow Bipole and Tripole", Medical and Biological Engineering and Computing, 35, No. 5, 1997, pp. 493-497.
Huff, Terry B. et al., "Real-Time CARS Imaging Reveals a Calpain-Dependent Pathway for Paranodal Myelin Retraction during High-Frequency Stimulation", PLoS ONE vol. 6, issue 3 (Mar. 3, 2011): e17176, 11 pgs.
Kent et al., "Instrumentation to Record Evoked Potentials for Closed-Loop Control of Deep Brain Stimulation", Conf. Proc. IEEE Eng. Med Biol. Sol, Aug. 2012, 10 pgs.
Kent et al., AR "Recording evoked potentials during deep brain stimulation: development and validation of instrumentation to suppress the stimulus artefact", J Neural Eng. Jun. 2012; 9 (3):036004, Apr. 18, 2012. doi: 10.1088/1741-2560/9/3/036004.
Kim et al., "A Wavelet-Based Method for Action Potential Detection From Extracellular Neural Signal Recording With Low Signal-to-Noise Ratio", IEEE Transactions on Biomedical Engineering, vol. 50, No. 8, Aug. 2003.
Kim et al., "Cell Type-specific Changes of the Membrane Properties of Peripherally-axotomized Dorsal Root Ganglion Neurons in a Rat Model of Neuropathic Pain", Neuroscience 86, No. 1 (May 21, 1998): 301-309, doi:10.1016/S0306-4522(98)00022-0.
Krames et al., "Neuromodulation", 1st Edition, Academic Press, 2009, pp. 540-541.
Krarup, Christian, "Compound sensory action potential in normal and pathological human nerves", Muscle & nerve, vol. 29, No. 4 (2004), pp. 465-483.
Krishnan et al., "Excitability Differences in Lower-Limb Motor Axons During and After Ischemia", Muscle & Nerve, vol. 31, No. 2 (2005), pp. 205-213.
Kumar et al., "Deep Brain Stimulation for Intractable Pain: a 15-year Experience", Neurosurgery, Issue 40, No. 4, Apr. 1997, pp. 736-747.
Kumar et al., "Double-blind evaluation of subthalamic nucleus deep brain stimulation in advanced Parkinson's disease", by the American Academy of Neurology, 51, No. 3, Sep. 1, 1998, pp. 850-855.
Kumar et al., "Globus Pallidus Deep Brain Stimulation for Generalized Dystonia: Clinical and PET Investigation", Neurology, 53, No. 4, 1999, pp. 871-874.
Laird et al., "A Model of Evoked Potentials in Spinal Cord Stimulation", IEEE Engineering in Medicine & Biology Society, 35th Annual Conference, Osaka, Japan: Jul. 3-7, 2013, pp. 6555-6558.
Lempka, Scott, "The Electrode-Tissue Interface During Recording and Stimulation in the Central Nervous System", published on May 2010.

(56) References Cited

OTHER PUBLICATIONS

Levy et al., "Incidence and Avoidance of Neurologic Complications with Paddle Type Spinal Cord Stimulation Leads", Neuromodulation 14(15), Sep. 2011, pp. 412-422.
Li S. et al., "Resonant antidromic cortical circuit activation as a consequence of high-frequency subthalamic deep-brain stimulation", J Neurophysiol. Dec. 2007; 98(6): 3525-3537, First published Oct. 10, 2007, doi:10.1152/jn.00808.2007.
Ma et al., "Similar Electrophysiological Changes in Axotomized and Neighboring Intact Dorsal Root Ganglion Neurons", Journal of Neurophysiology 89, No. 3 (Mar. 1, 2003), pp. 1588-1602, doi:10.1152/jn.00855.2002.
Macefield, "Spontaneous and Evoked Ectopic Discharges Recorded from Single Human Axons", Muscle & Nerve 21, No. 4, Apr. 1998, pp. 461-468.
Mahnam, A. et al. "Measurement of the Current-Distance Relationship Using a Novel Refractory Interaction Technique", J. Neural Eng. 6, 2009, 22 pgs.
Markandey, Vishal, "ECG Implementation on the TMS320C5515 DSP Medical Development Kit (MDK)", Texas Instruments Application Report Jun. 2010, 35 pgs.
European Search Report for European Application 12785619.3 Search completed Oct. 13, 2014, dated Oct. 23, 2014, 7 pgs.
European Search Report for European Application 12785669.8 Search completed Sep. 22, 2014, dated Sep. 29, 2014, 5 pgs.
Extended European Search Report for EP Application 12785483.4 completed Sep 16, 2014, 7 pgs.
Extended European Search Report for European Application No. 11820923.8, report completed Dec. 9, 2013, report dated Dec. 17, 2013, 6 pgs.
Extended European Search Report for European Application No. 13852669.4, search completed Jun. 8, 2016, dated Jun. 22, 2016, 9 pgs.
Extended European Search Report for European Application No. 14861553.7, search completed Jun. 8, 2017, dated Jun. 19, 2017, 8 pgs.
Extended European Search Report for European Application No. 14863597.2, search completed Jun. 6, 2017, dated Jun. 13, 2017, 9 pgs.
Extended European Search Report for European Application No. 15768956.3, search completed Oct. 3, 2017, dated Oct. 10, 2017, 8 pgs.
Extended European Search Report for European Application No. 13853514.1, search completed Jun. 8, 2016, dated Jun. 15, 2016, 7 pgs.
International Preliminary Report on Patentability for International Application No. PCT/AU2011/001127, report dated Mar. 5, 2013, 9 pgs.
International Preliminary Report on Patentability for International Application No. PCT/AU2012/000511, report dated Nov. 19, 2013, 6 pgs.
International Preliminary Report on Patentability for International Application No. PCT/AU2012/000512, report dated Nov. 19, 2013, 8 pgs.
International Preliminary Report on Patentability for International Application No. PCT/AU2012/000513, report dated Nov. 19, 2013, 11 pgs.
International Preliminary Report on Patentability for International Application No. PCT/AU2012/000515, report dated Nov. 19, 2013, 5 pgs.
International Preliminary Report on Patentability for International Application No. PCT/AU2012/000516, report dated Nov. 19, 2013, 9 pgs.
International Preliminary Report on Patentability for International Application No. PCT/AU2012/000517, report dated Nov. 19, 2013, 6 pgs.
International Preliminary Report on Patentability for International Application No. PCT/AU2012/000518, report dated Nov. 19, 2013, 11 pgs.
International Preliminary Report on Patentability for International Application No. PCT/AU2012/001441, report dated May 27, 2014, 10 pgs.
International Preliminary Report on Patentability for International Application No. PCT/AU2013/001279, report dated May 12, 2015, 6 pgs.
International Preliminary Report on Patentability for International Application No. PCT/AU2013/001280, report dated May 12, 2015, 6 pgs.
International Preliminary Report on Patentability for International Application No. PCT/AU2014/001049, report dated May 17, 2016, 5 pgs.
International Preliminary Report on Patentability for International Application No. PCT/AU2014/050369, report dated May 24, 2016, 8 pgs.
International Preliminary Report on Patentability for International Application No. PCT/AU2015/050135, report dated Oct. 4, 2016, 13 pgs.
International Preliminary Report on Patentability for International Application No. PCT/AU2015/050215, report dated Nov. 8, 2016, 4 pgs.
International Preliminary Report on Patentability for International Application No. PCT/AU2015/050422, report dated Jan. 31, 2017, 8 pgs.
International Preliminary Report on Patentability for International Application No. PCT/AU2015/050724, report dated May 23, 2017, 5 pgs.
International Preliminary Report on Patentability for International Application No. PCT/AU2015/050753, report dated Jun. 13, 2017, 7 pgs.
Extended European Search Report for European Application No. 17778477.4, report completed Nov. 12, 2019, dated Nov. 20, 2019, 7 pgs.
Extended European Search Report for European Application No. 17814341.8, report completed Dec. 12, 2019, report dated Jan. 2, 2020, 8 pgs.
International Preliminary Report on Patentability for International Application No. PCT/AU2018/050278, dated Sep. 29, 2020, 7 pgs.
International Preliminary Report on Patentability for International Application No. PCT/AU2019/050384, dated Oct. 27, 2020, 8 pgs.
International Search Report and Written Opinion for International Application No. PCT/AU2018/050278, Search completed Jun. 18, 2018, dated Jun. 18, 2018, 12 Pgs.
International Search Report and Written Opinion for International Application No. PCT/AU2019/050384, Search completed Jun. 25, 2019, dated Jun. 25, 2019, 15 Pgs.
Japanese Office Action for Application No. 2017-546830, dated Feb. 20, 2020, 5 pages with English translation.
Japanese Office Action for Application No. 2017-553090, dated Mar. 16, 2020, 12 pages with English translation.
Japanese Office Action for Application No. 2018-513699, dated Jun. 8, 2020, 7 pages with English translation.
Office Action for Chinese Patent Application No. 201680020725.4, dated Mar. 16, 2020, 8 pgs.
Kopelman et al., "Attempted Reversible Sympathetic Ganglion Block by an Implantable Neurostimulator", Interactive CardioVascular and Thoracic Surgery, Feb. 7, 2012, vol. 14, Issue 5, pp. 605-609, doi:10.1093/icvts/ivr137.

METHOD AND APPARATUS FOR ESTIMATING NEURAL RECRUITMENT

CROSS-REFERENCE TO RELATED APPLICATIONS

This application claims the benefit of U.S. patent application Ser. No. 14/117,152 filed Nov. 12, 2013, which is the National Stage of International Application No. PCT/AU2012/000517 filed May 11, 2012, which claims the benefit of Australian Provisional Patent Application No. 2011901827 filed 13 May 2011 and Australian Provisional Patent Application No. 2011901817 filed 13 May 2011, all of which are incorporated herein by reference.

TECHNICAL FIELD

The present invention relates to measuring a neural response to a stimulus, and in particular relates to measurement of a compound action potential by using one or more electrodes implanted proximal to the neural pathway, in order to estimate neural recruitment resulting from an applied stimuli.

BACKGROUND OF THE INVENTION

There are a range of situations in which it is desirable to apply neural stimuli in order to give rise to a compound action potential (CAP). For example, neuromodulation is used to treat a variety of disorders including chronic pain, Parkinson's disease, and migraine. A neuromodulation system applies an electrical pulse to tissue in order to generate a therapeutic effect. When used to relieve chronic pain, the electrical pulse is applied to the dorsal column (DC) of the spinal cord. Such a system typically comprises an implanted electrical pulse generator, and a power source such as a battery that may be rechargeable by transcutaneous inductive transfer. An electrode array is connected to the pulse generator, and is positioned in the dorsal epidural space above the dorsal column. An electrical pulse applied to the dorsal column by an electrode causes the depolarisation of neurons, and generation of propagating action potentials. The fibres being stimulated in this way inhibit the transmission of pain from that segment in the spinal cord to the brain. To sustain the pain relief effects, stimuli are applied substantially continuously, for example at 100 Hz.

While the clinical effect of spinal cord stimulation (SCS) is well established, the precise mechanisms involved are poorly understood. The DC is the target of the electrical stimulation, as it contains the afferent Aβ fibres of interest. Aβ fibres mediate sensations of touch, vibration and pressure from the skin, and are thickly myelinated mechanoreceptors that respond to non-noxious stimuli. The prevailing view is that SCS stimulates only a small number of Aβ fibres in the DC. The pain relief mechanisms of SCS are thought to include evoked antidromic activity of Aβ fibres having an inhibitory effect, and evoked orthodromic activity of Aβ fibres playing a role in pain suppression. It is also thought that SCS recruits Aβ nerve fibres primarily in the DC, with antidromic propagation of the evoked response from the DC into the dorsal horn thought to synapse to wide dynamic range neurons in an inhibitory manner.

Neuromodulation may also be used to stimulate efferent fibres, for example to induce motor functions. In general, the electrical stimulus generated in a neuromodulation system triggers a neural action potential which then has either an inhibitory or excitatory effect. Inhibitory effects can be used to modulate an undesired process such as the transmission of pain, or to cause a desired effect such as the contraction of a muscle.

The action potentials generated among a large number of fibres sum to form a compound action potential (CAP). The CAP is the sum of responses from a large number of single fibre action potentials. The CAP recorded is the result of a large number of different fibres depolarising. The propagation velocity is determined largely by the fibre diameter and for large myelinated fibres as found in the dorsal root entry zone (DREZ) and nearby dorsal column the velocity can be over 60 ms$^{-1}$. The CAP generated from the firing of a group of similar fibres is measured as a positive peak potential P1, then a negative peak N1, followed by a second positive peak P2. This is caused by the region of activation passing the recording electrode as the action potentials propagate along the individual fibres. An observed CAP signal will typically have a maximum amplitude in the range of microvolts, whereas a stimulus applied to evoke the CAP is typically several volts.

To resolve a 10 µV SCP with 1 µV resolution in the presence of an input 5V stimulus, for example, requires an amplifier with a dynamic range of 134 dB, which is impractical in implant systems. As the neural response can be contemporaneous with the stimulus and/or the stimulus artefact, CAP measurements are difficult to obtain. This is particularly so for pain relief where patients typically obtain best effects with a pulse width in the range of 100-500 µs which ensures much of the neural response occurs while the stimulus is still ongoing, making measurement of the neural response effectively impossible.

For effective and comfortable operation, it is necessary to maintain stimuli amplitude or delivered charge above a recruitment threshold, below which a stimulus will fail to recruit any neural response. It is also necessary to apply stimuli which are below a comfort threshold, above which uncomfortable or painful percepts arise due to increasing recruitment of Aδ fibres which are thinly myelinated sensory nerve fibres associated with acute pain, cold and pressure sensation. In almost all neuromodulation applications, a single class of fibre response is desired, but the stimulus waveforms employed can recruit other classes of fibres which cause unwanted side effects, such as muscle contraction if motor fibres are recruited. The task of maintaining appropriate stimulus amplitude is made more difficult by electrode migration and/or postural changes of the implant recipient, either of which can significantly alter the neural recruitment arising from a given stimulus, depending on whether the stimulus is applied before or after the change in electrode position or user posture. Postural changes alone can cause a comfortable and effective stimulus regime to become either ineffectual or painful.

Another control problem, faced by neuromodulation systems of all types, is achieving neural recruitment at a sufficient level required for therapeutic effect, but at minimal expenditure of energy. The power consumption of the stimulation paradigm has a direct effect on battery requirements which in turn affects the device's physical size and lifetime. For rechargeable systems, increased power consumption results in more frequent charging and, given that batteries only permit a limited number of charging cycles, ultimately this reduces the lifetime of the device.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY OF THE INVENTION

According to a first aspect the present invention provides a method of estimating neural recruitment arising from a selected neural stimulus, the method comprising:
applying the selected neural stimulus;
after the selected neural stimulus, applying a probe stimulus having a short pulse width;
measuring a remnant neural response evoked by the probe stimulus; and
from the remnant neural response, estimating neural recruitment caused by the selected neural stimulus.

According to a second aspect the present invention provides an implantable device for estimating neural recruitment arising from a selected neural stimulus, the device comprising:
a plurality of electrodes including one or more nominal stimulus electrodes and one or more nominal sense electrodes;
a stimulus source for providing stimuli to be delivered from the one or more stimulus electrodes to neural tissue;
measurement circuitry for obtaining a measurement of a neural signal sensed at the one or more sense electrodes; and
a control unit configured to control application of a selected stimulus to neural tissue using the stimulus electrodes; the control unit further configured to, after the selected neural stimulus, apply a probe stimulus having a short pulse width; the control unit further configured to measure a remnant neural response evoked by the probe stimulus; and the control unit further configured to estimate from the remnant neural response a neural recruitment caused by the selected neural stimulus.

The present invention thus provides for probing of an un-recruited fibre population which was not recruited by the selected stimulus, by reference to which an understanding of the population recruited by the selected stimulus can be obtained.

Embodiments of the invention may be particularly beneficial in providing for estimation of neural recruitment effected by a selected stimulus having a long pulse width, for example in the range of 100-500 µs, in relation to which it is not possible to directly measure a neural response due to temporal overlap of the stimulus and response.

In preferred embodiments, the probe stimulus is applied quickly after the selected stimulus, within the refractory period of the fibres recruited by the selected stimulus.

In some embodiments, a second probe stimulus is applied after the refractory period of fibres recruited by either the selected stimulus or the probe stimulus, and a second measure of evoked neural response is obtained as caused by the second probe stimulus. In such embodiments, the neural recruitment arising from the selected neural stimulus may be estimated by comparing the remnant neural response to the second measure.

Additionally or alternatively, some embodiments may comprise:
a) applying the probe stimulus at a time t after conclusion of the selected stimulus;
b) obtaining a measure of a remnant neural response arising from the probe stimulus;
c) changing t; and
d) repeating (a), (b) and (c) to determine variations in the remnant neural response measure, with varying t.

For example, with increasing t an increase in the remnant neural response may indicate the refractory period of the fibre population recruited by the selected stimulus.

In embodiments of the invention in which an estimate of refractory period is obtained, the refractory period may be monitored over time in order to diagnose onset or progression of a disease.

According to another aspect the present invention provides a computer program product comprising computer program code means to make a computer execute a procedure for estimating neural recruitment arising from a selected neural stimulus, the computer program product comprising computer program code means for carrying out the method of the first aspect.

BRIEF DESCRIPTION OF THE DRAWINGS

An example of the invention will now be described with reference to the accompanying drawings, in which.

DESCRIPTION OF THE PREFERRED EMBODIMENTS

Figure 1:
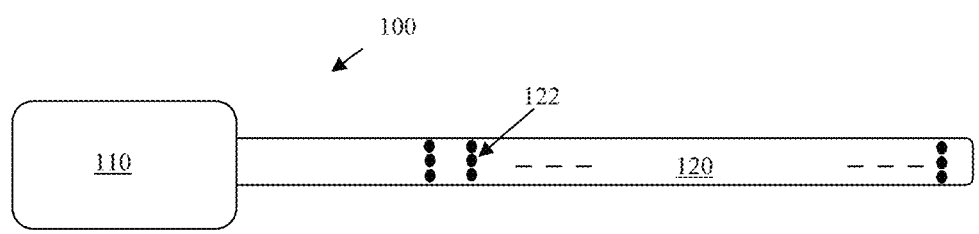
FIG. 1 illustrates an implantable device suitable for implementing the present invention.

FIG. 1 illustrates an implantable device 100 suitable for implementing the present invention. Device 100 comprises an implanted control unit 110, which controls application of neural stimuli, and controls a measurement process for obtaining a measurement of a neural response evoked by the stimuli from each of a plurality of electrodes. Device 100 further comprises an electrode array 120 consisting of a three by eight array of electrodes 122, each of which may be selectively used as either the stimulus electrode or sense electrode, or both.

Figure 2:
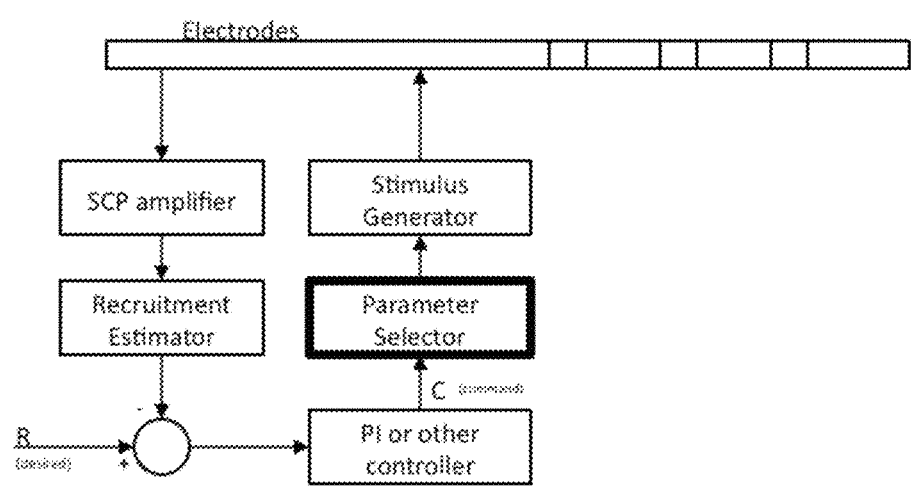
FIG. 2 is a schematic of a feedback controller which refines future stimuli based on estimated recruitment of neurons by past stimuli.

FIG. 2 is a schematic of a feedback controller which refines future stimuli based on estimated recruitment of neurons by past stimuli. The present embodiment provides for the recruitment estimator in FIG. 2 to obtain a measurement of a masked neural response arising in response to a probe stimuli applied during a refractory period of a therapeutic stimulus, and also provides for measurement of an unmasked neural response arising in response to a probe stimuli applied after a refractory period of the same or equivalent subsequent therapeutic stimulus. Comparing the ratio or difference between the masked and unmasked neural responses indicates a level of recruitment achieved by the therapeutic stimulus.

In this embodiment the evoked CAP measurements are made by use of the neural response measurement techniques set out in the Australian provisional patent application No. 2011901817 in the name of National ICT Australia Ltd entitled "Method and apparatus for measurement of neural response" from which the present application claims priority.

Figure 3:
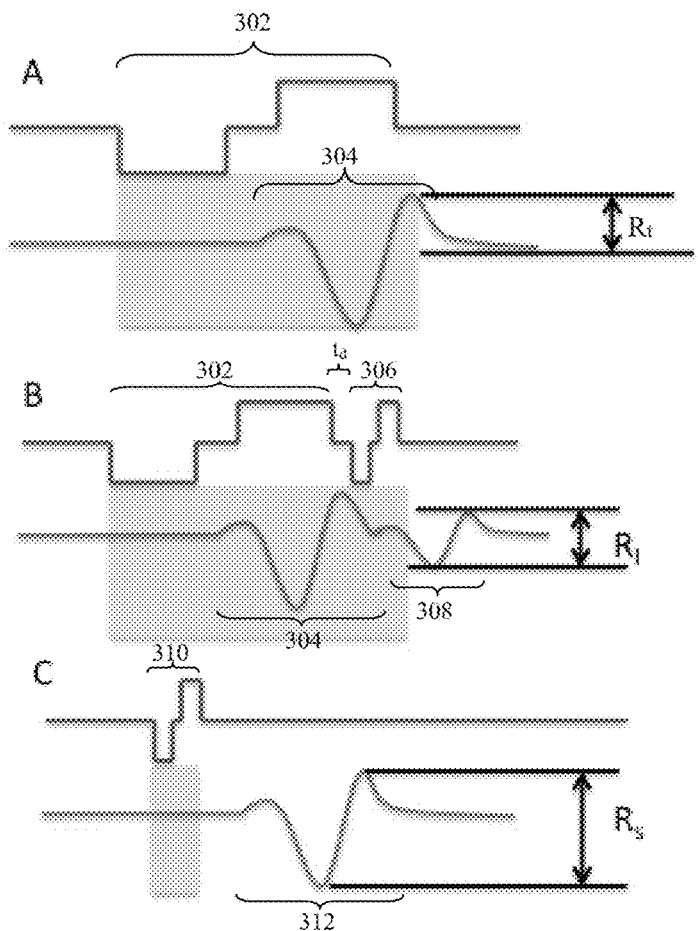
FIG. 3 illustrates the masked to unmasked stimulation paradigm provided by the present embodiment of the invention.

Long pulse widths on the order of 400 µs, as used in many commercially available stimulators, cause problems for the measurement of evoked response, as much of the neural response passes the recording electrodes during the stimulus period. That is, in such a biphasic pulse, at least 0.8 ms passes from stimulus onset before measurement is possible. As shown in FIG. 3a, the therapeutic stimulus 302 continues for a sufficiently long period of time that it substantially temporally overlaps the evoked neural response 304. The signal amplitudes in FIG. 3 are not to scale, and the therapeutic stimulus is of the order of volts while the neural response measurement is of the order of tens of microvolts, so that in the case shown in FIG. 3a the evoked response is practically impossible to measure directly. Nevertheless, for many reasons it is desirable to measure or estimate the amplitude of the response $R_I$ induced by stimulus 302.

FIGS. 3b and 3c illustrate the masked to unmasked stimulation paradigm provided by the present embodiment of the invention. In order to estimate how many fibres are recruited in the neural response 304 arising from the long therapeutic pulse 302, a shorter probe pulse 306 is delivered shortly after the therapeutic stimulus 302. The neural response 308 caused by probe pulse 306 is not contemporaneous with any stimulus, and is therefore able to be measured without being swamped by large stimulus voltages. Notably, by delivering the probe pulse 306 during the refractory period of the fibres triggered in response 304, the response 308 has an amplitude $R_I$ which is proportional to the number of fibres which were not triggered by the long pulse 302.

After a time delay of sufficient length to allow all fibres triggered as part of either response 304 or response 308 to exit their refractory states, another short probe pulse 310 is delivered as shown in FIG. 3c. Probe pulse 310 preferably has the same parameters as probe pulse 306. Obtaining a measure of response 312 provides an unmasked response amplitude measurement $R_S$, with $R_S > R_I$, against which the first, masked response 308 can be compared. This masked/unmasked ratio $(R_I : R_S)$ can be used to estimate what proportion of the accessible fibre population was stimulated in response 304 by therapeutic stimulus 302, thereby allowing $R_t$ to be estimated. Notably, when performed sufficiently quickly that a fibre-to-electrode distance will remain substantially constant, this technique is not susceptible to the problem of unknown fibre-to-electrode distance as the ratios cancel the effect of variable electrode-to-fibre distance.

In addition to determining recruitment of long pulse width stimuli, it can be useful to measure physiological parameters such as refractory periods in order to give a diagnosis of various conditions or diseases. Thus, in another embodiment of the invention the refractory period is estimated by first obtaining a measure $R_S$ of the unmasked neural response to a given probe stimulus. Then, two stimuli are applied close together separated by a variable delay $t_d$ (FIG. 3b). With increasing $t_d$, the amplitude $R_I$ can be expected to markedly increase when the onset of pulse 306 is delayed sufficiently to allow the average refractory period of the neural population recruited in response 304 to conclude, so that observing such an increase in $R_I$ allows that population's refractory period to be estimated. There are a number of neurological conditions and non-neurological conditions which can affect the refractory period. This measurement technique may thus serve as a useful diagnostic indicator.

Figure 4:
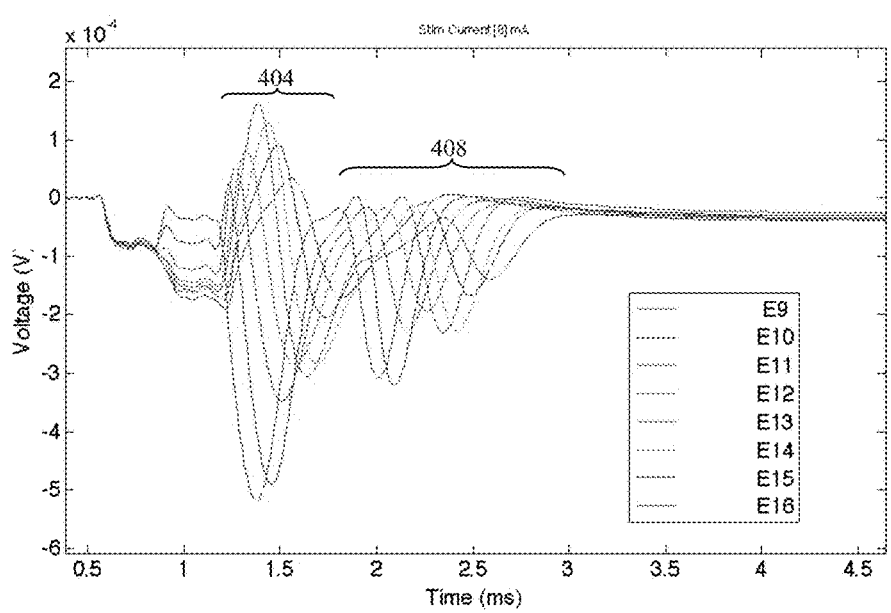
FIG. 4 illustrates recordings of actual evoked responses in accordance with the method of one embodiment of the present invention.

FIG. 4 illustrates recordings of actual evoked responses in accordance with the embodiment of FIG. 3. The recordings of a response pair were made on 8 spaced apart electrodes along the spinal column as the evoked responses 404, 408 travelled along the spinal column adjacent to the array. As can be seen, an initial response 404 is evoked by a first stimulus, and then a second response 408 is evoked immediately afterwards in the refractory period of the neural population recruited as part of response 404. Response 408 is of reduced, but non-zero, amplitude. The relative ratios of the amplitudes of the measurements of the two responses thus permit the above-described information to be elicited.

Figure 5:
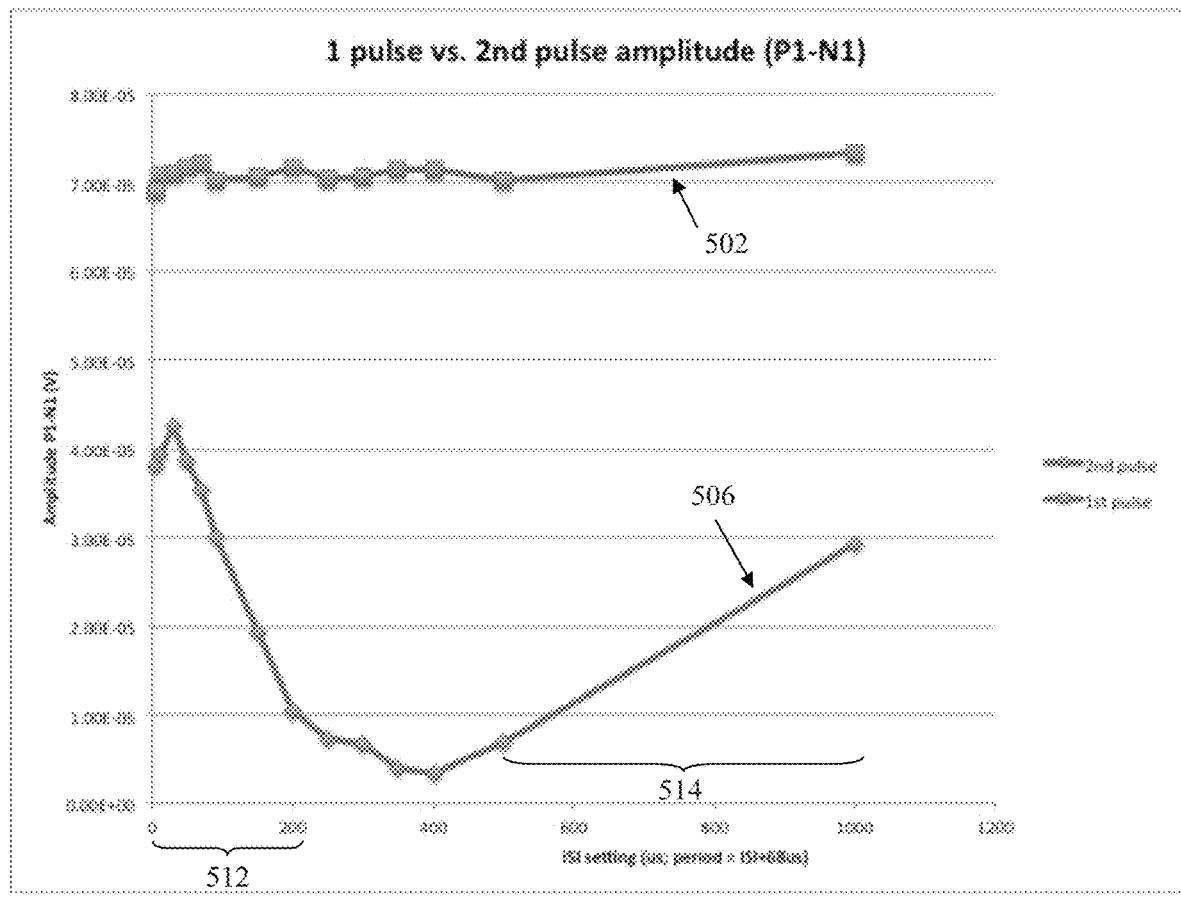
FIG. 5 is a plot of the (P1-N1) amplitude of measurements of responses evoked by two pulses, for varying inter-stimulus interval.

FIG. 5 is a plot of the (P1-N1) amplitude of measurements of responses 502, 506 respectively evoked by a first pulse 302 and a second pulse 306 of equal amplitude and pulse width, for varying inter-stimulus interval $t_d$. As can be seen at 502, the first pulse 302 produces the same recruitment and response amplitudes irrespective of $t_d$. However, the recruitment effected by the second pulse 306 varies considerably with $t_d$, as shown by 506. Two fibre population characteristics are evident in this plot, either or both of which may be investigated in accordance with the present invention in order to determine suitable stimulus parameters and/or physiological state or change. First, pulse 302 will depolarise some fibres close to threshold, but without activating them. This partial depolarisation means that for small $t_d$, in the range (512) of about 0 to 200 µs, where pulse 306 is sufficiently close in time to pulse 302, some fibres that had not been activated by 302 may be activated by 306 more easily than is the case for the remainder of the refractory period for $t_d > 200$ µs. This depolarisation will decay with time, usually to resting levels before the end of the absolute refractory period for the fibres that were activated by 302. This means for short inter-stimulus intervals (e.g. <200 us), there will be a response 308 from fibres which had residual depolarisation from 302. Second, for $t_d$ greater than about 400 µs, a relative refractory period 514 commences, during which fibres activated by 302 gradually become able to be activated again. Between the remnant depolarisation period 512 and the relative refractory period 514, the absolute refractory period dominates and the second pulse 306 is almost entirely unable to recruit any response (it is noted that curve 506 is at levels around 5 µV in this period which may be noise and does not necessarily indicate any response has been evoked). Thus assessing curve 506 instantaneously permits a current state of both (a) the residual depolarisation decay 512, and (b) onset of the relative refractory period 514 to be assessed. Monitoring curve 506 over time permits changes in these characteristics to be determined, for example to be used for feedback to optimise therapeutic stimuli or in order to diagnose or monitor an underlying disease.

While FIG. 3b shows the probe pulse 306 as having the same amplitude as therapeutic pulse 302, alternative embodiments may advantageously use probe pulses 306 and/or 310 which are of a different amplitude to therapeutic pulse 302. For example, therapeutic pulse 302 is usually set to a comfortable level for the patient, and at such a level not all fibres are usually recruited by pulse 302. Pulse 306 may therefore be set to have a greater amplitude and/or a greater total charge than therapeutic stimulus 302 in order to ensure that the probe pulse 306 will recruit at least some fibres even when applied during the refractory period of fibres recruited as part of response 304.

In another embodiment the probe stimulus 306 may be configured to have reduced recruitment capability as compared to pulse 302, so that if pulse 306 is applied during the absolute refractory period of fibres recruited as part of response 304 then pulse 306 will recruit no additional response. In such embodiments, when the relative delay $t_d$ is such that probe stimulus 306 occurs in the relative refractory period of response 304, being the period in which some fibres recruited as part of response 304 have concluded their refractory period but some have not, then the probe stimulus response 308 will begin to recruit fibres. Determining the value of $t_d$ at which a threshold exists for response 308 starting to arise provides useful information regarding the refractory period of response 304.

Routinely, during assessment of patients for spinal cord stimulation therapy, the patient will undergo a trial stimulation procedure. This is where the patient is implanted with a percutaneous lead with an externalised set of contacts. The lead is attached to an external pulse generator and the patient has use of the device for several days. At the end of the trial period the clinician and patient assess the performance of the system with regard to pain relief and a choice is made whether or not to proceed with a full implantation. The take-home device for trial purposes may consist of both a stimulus generator but also an evoked response measurement system. The ERT responses recorded during the trial period could be used to adjust the stimulus parameters as described above.

The ERT system measures amplitude growth functions etc., collected at time of surgery and during the trial stimulation period, and together with subjective performance measures could be used to develop a correlation between the response parameters and the patient outcomes. For instance, there is considerable variation in threshold response and there may exist a correlation between threshold and outcome where lower thresholds generate better outcomes. There are a large number of neurological parameters that can be collected in performing ERT measures, including refractory periods. Systematic collection of this data across a number of patients will allow analysis for correlation with outcome.

It will be appreciated by persons skilled in the art that numerous variations and/or modifications may be made to the invention as shown in the specific embodiments without departing from the spirit or scope of the invention as broadly described. For example the neural response measurement may be conducted in accordance with any suitable CAP measurement technique. The present embodiments are, therefore, to be considered in all respects as illustrative and not restrictive.

The invention claimed is:

1. A method of determining neural recruitment arising from a selected neural stimulus, the method comprising:
    applying the selected neural stimulus from at least one stimulus electrode;
    after applying the selected neural stimulus, and within a refractory period of fibres recruited by the selected neural stimulus, applying a probe stimulus having a short pulse width;
    measuring, with measurement circuitry, a remnant neural response evoked by the probe stimulus; and
    a control unit determining from the remnant neural response a neural recruitment caused by the selected neural stimulus.

2. The method of claim 1, wherein the selected neural stimulus has a pulse width in the range of 100-500 µs.

3. The method of claim 1, further comprising applying a second probe stimulus after the refractory period of fibres recruited by either the selected neural stimulus or the probe stimulus, and obtaining a second measure of evoked neural response as caused by the second probe stimulus.

4. The method of claim 3 further comprising determining the neural recruitment arising from the selected neural stimulus by comparing the remnant neural response to the second measure.

5. The method of claim 1 further comprising:
    applying the probe stimulus at a time t after conclusion of the selected neural stimulus;
    obtaining a measure of a remnant neural response arising from the probe stimulus;
    changing t; and
    repeating the applying the probe stimulus, the obtaining the measure of the remnant neural response, and the changing t, to determine variations in the remnant neural response measure, with varying t.

6. The method of claim 5 further comprising identifying a value $t_r$ at which an increase in the remnant neural response with increasing t arises, and taking $t_r$ as an estimate for a refractory period of the fibre population recruited by the selected neural stimulus.

7. The method of claim 1 further comprising monitoring a refractory period over time in order to diagnose onset or progression of a disease.

8. An implantable device for determining neural recruitment arising from a selected neural stimulus, the implantable device comprising:
    a plurality of electrodes including one or more stimulus electrodes and one or more sense electrodes;
    a stimulus source for providing stimuli to be delivered from the one or more stimulus electrodes to neural tissue;
    measurement circuitry for obtaining a measurement of a neural signal sensed at the one or more sense electrodes; and
    a control unit configured to control application of a selected stimulus to neural tissue using the one or more stimulus electrodes; the control unit further configured to, after the selected neural stimulus, and within a refractory period of fibres recruited by the selected neural stimulus, apply a probe stimulus having a short pulse width; the control unit further configured to measure a remnant neural response evoked by the probe stimulus; and the control unit further configured to determine from the remnant neural response a neural recruitment caused by the selected neural stimulus.

9. The implantable device of claim 8, wherein the selected neural stimulus has a pulse width in the range of 100-500 µs.

10. The implantable device of claim 8 wherein the control unit is further configured to apply a second probe stimulus after the refractory period of fibres recruited by either the selected neural stimulus or the probe stimulus, and to obtain a second measure of evoked neural response as caused by the second probe stimulus.

11. The implantable device of claim 10 wherein the control unit is further configured to determine the neural recruitment arising from the selected neural stimulus by comparing the remnant neural response to the second measure.

12. The implantable device of claim 8 wherein the control unit is further configured to: apply the probe stimulus at a time t after conclusion of the selected neural stimulus; obtain a measure of a remnant neural response arising from the probe stimulus; change t; and, repeat the applying the probe stimulus, the obtaining the measure of the remnant neural response and the changing t to determine variations in the remnant neural response measure, with varying t.

13. The implantable device of claim 12 wherein the control unit is further configured to identify a value $t_r$ at which an increase in the remnant neural response with increasing t arises, and take $t_r$ as an estimate for a refractory period of the fibre population recruited by the selected neural stimulus.

14. The implantable device of claim 8 wherein the control unit is further configured to monitor a refractory period over time in order to diagnose onset or progression of a disease.

\* \* \* \* \*